United States Patent [19]

Swenson

[11] Patent Number: Plant 5,716

[45] Date of Patent: Apr. 15, 1986

[54] GRAPEVINE

[75] Inventor: Elmer Swenson, Osceola, Wis.

[73] Assignee: Swenson-Smith Vines Inc., Excelsior, Minn.

[21] Appl. No.: 645,336

[22] Filed: Aug. 29, 1984

[51] Int. Cl.[4] ..... A01H 5/03

[52] U.S. Cl. ..... Plt./47

[58] Field of Search ..... Plt./47

*Primary Examiner*—Robert E. Bagwill

[57] ABSTRACT

A grapevine which exhibits excellent cultural characteristics such as resistance to mildew, winter hardiness down to −28° Fahrenheit, open canopy, and grapes which produce an excellent white wine which is absent of labrusca flavor and aroma typical of such hardy varieties.

3 Drawing Figures

ORIGIN AND REPRODUCTION

The present invention relates to a new and distinct variety of grapevine which has been produced by me as a result of an ungoing grape breeding program at my vineyard and nursery located in Polk County, near Osceola, in northern Wisconsin. This variety has also been secondary tested at my corporation's (Swenson-Smith Vines, Inc.) secondary testing sites located in Minnesota. The present variety is characterized by good winter hardiness and usefulness as a winegrape, having desirable aroma, flavor, acidity and sugar content, with no foxiness or labrusca flavor or aroma.

For some 40 years, I have been growing a large number of grapevines at my above-noted nursery and vineyard directed to the production of grapevines having the desirable winter hardiness for northern states and commercially useful as wine and/or table grapes.

By way of background, it is noted that there have been very few desirable commercial grape varieties for growing in the harsh northern climate of Minnesota, Wisconsin, and similar northern states. While this northern region has a summer thermal accumulation similar to that of the best grape growing areas of the world, the low winter temperatures have generally prevented development of vineyards in this region because of the lack of suitably hardy grape varieties.

Current vineyard cultural practices in the noted northern region generally involve early fall pruning, after which the vines are removed from trellises and laid upon the ground and covered for wintering. In the spring, the vines are uncovered and re-trellised, all of which involves labor costs, which are generally prohibitive and make it quite difficult for northern vineyards in such climates in operate profitably. Accordingly, for grapevines to be of high commercial value to vineyards in such northern regions, such as Minnesota and Wisconsin, it has been nearly essential that the varieties be hardy enough to remain on the trellises throughout the winter months without removal and winter covering. The present variety has this characteristic for southernmost portion of some northern tier states.

This new variety of grapevine was selected by me for its combination of good winter hardiness and usefulness as a wine grape, producing a good white wine. When blended in the proper ratio with Seyval, it has placed the Seyval first in international competition.

The present variety is a result of my breeding program, in which my varietal selections are designated by number with the prefix ES. This variety is a select seedling resulting from a cross of Edelweiss×S.V. 12-375. While under test, I have identified the present variety as ES422 and now select the name "Esprit" therefor.

I have reproduced the present variety by means of cuttings and have carefully observed the variety for several years. The continual observation and testing of the present variety has convinced me that it is a new and improved cultivar of grapevine, as indicated by the following and unique combination of outstanding qualities which distinguish this variety from all other varieties of grapevine known to me.

SUMMARY OF CHARACTERISTICS

The unique combination of characteristics of the present variety ES422, named "Esprit", are as follows:

1. Winter hardiness. The present variety has good winter hardiness for certain vineyard zones which experience losses due to lack of winter hardiness. For example, some losses were experienced by many Ohio vineyards in 1984. More specifically, this variety has survived on trellises with a winter temperature of −28° Fahrenheit with little apparent injury to its vines and approximately fifty percent bud injury. Such survival has been at my vineyard located near Osceola, Wis. and at a secondary site located near Excelsior, Minn.

2. Low Acidity. The present variety has also produced grapes of relatively low acidity for a cold climate grape, a desirable attribute for wine grapes. In years of relatively poor growing conditions, this vine's acidity has averaged 1.01% and in years of good growing conditions its acidity has averaged 0.92%.

3. Sugar Content. This cultivar has an average sugar of 18.1% in its most northern test site, and in its most southern site near Excelsior, Minn. it averages a brix or sugar content of 19.5%.

4. Flavor and Color. The typical foxiness or labrusca flavor and aroma which is an objectionable characteristic generally for wine grapes, yet is typical of previous varieties having good winter hardiness, is not apparent in this variety. The variety produces a white wine we feel is superior to many of the German white wines.

SEXUAL REPRODUCTION

The present variety has been asexually reproduced by me by means of vine cuttings at my nursery and vineyard in Polk County, near Osceola, Wis. Such asexual reproduction confirms that the characteristics and qualities stated herein for this vine variety are true to form and consistent through succeeding propagation.

DETAILED DESCRIPTION

The accompanying drawings comprise photographs showing characteristics of this new variety. The photographs were taken of specimens of the variety growing at two Swenson-Smith Vines, Inc. test sites, at Mr. David MacGregor's site near South Haven, Minn. and at Mr. William Smith's site near Excelsior, Minn. The color photographs depict color features as true as reasonably possible.

FIG. 1 is a color photograph showing the form and growth of a mature vine of the present variety.

FIG. 2 is a color photograph showing the mature summer leaf form for typical leaves of this variety. FIG. 3 is a color photograph showing typical fruit clusters of the present variety.

The following is a detailed description or specification of the pomological characteristics of this new variety, with color terminology or references in accordance with The Royal Horticulture Society Colour Chart. Where dimensions, sizes, colors, and other characteristics are given, it is to be understood that the same are approximations of averages as they appear under conditions prevailing at our secondary test sites as well as at my vineyard near Osceola, Wis.

Vine:

*Growth habit.*—Very open canopy with canes not upright as a typical Vinifera grape vine but more trailing. Medium vigor.

*Trunk.*—Thick and sheds bark in long strips. The trunk needs support. Inner bark color is closest to Greyed Orange Color Group 166C.

*Canes.*—Purple shoots with light labrusca hair. Tendrils are intermittent (skip every third node) with tri-forked tendrils common.

Foliage:

*Leaves.*—Young growing tip of budding leaves are felty with a whitish green color with a very slight rose margin. Very young leaves are copper above and have a cobwebby appearance underneath. The mature leaf has large pointed teeth; open lyre shaped petiolar sinus; downy tufts at the bifurcation of veins of leaf underside; Mature leaf often entire but at times slightly trilobed. Top mature leaf color is between Yellow Green Group 147A and 137A; Leaf underside is closest to color Group 147B; at harvest petiole is Greyed Purple Group 183C. Leaf veins belong to Yellow Green Group 144D. The average mature leaf is approximately 10 centimeters wide by 10 centimeters long.

Grapes:

*Maturity.*—Mid-season to Late Mid-season or Mid-September to late September at Excelsior, Minn.

*Size of berry.*—Natural size ranges in diameter from 1.2 centimeters to 1.7 centimeters with the average diameter being 1.5 centimeters. Berries are spherical in shape.

*Ripening.*—Ripens somewhat evenly. Fruit holds well on the vine with no shattering.

*Color of the berry.*—Closest to Yellow Green Group 146D (at only 14.1 Brix).

*Cluster.*—Medium packed; definitely not tightly packed. General cluster shape is cone shaped. Medium clusters which measure: 6.5 centimeter stem; 10.9 centimeter cluster width; 14.6 centimeters in length. Average cluster weight is approximately 8 oz. Large clusters may reach one pound with sixty to ninety berries per cluster.

*Seed.*—2.7 average seeds per berry. Seed color is reddish brown.

*Pulp.*—Juicey. Color closest to Yellow Green 150D.

*Juice color.*—Free run juice is close to Green White 157B to 157C.

*Sugar and acid.*—19.0 percent sugar and 1.01 acid on Sept. 21, 1983 at Excelsior, Minn. vine site.

*Clusters per shoot.*—2 per shoot average.

*Other characteristics.*—Excellent resistance to Downy mildew and somewhat resistant to black rot at sites tested. Perfect flowers. The fruit has superior fruitiness and freshness and as an approximate 20% blend with the Seyval appears to produce a wine superior to the Seyval. Such a blend gained first place in the 1983 International Homewinemakers Event at Sacramento, Calif.

I claim:

1. A new and distinct variety of grapevine, substantially as shown and described herein, characterized particularly as to novelty by the unique combination of winter hardiness down to −28° Fahrenheit, producing white grapes which have produced superior wine, and grapes with relatively low acidity, average sugar content and a flavor and aroma absent from the typical foxiness or labrusca usually found in such hardy varieties.

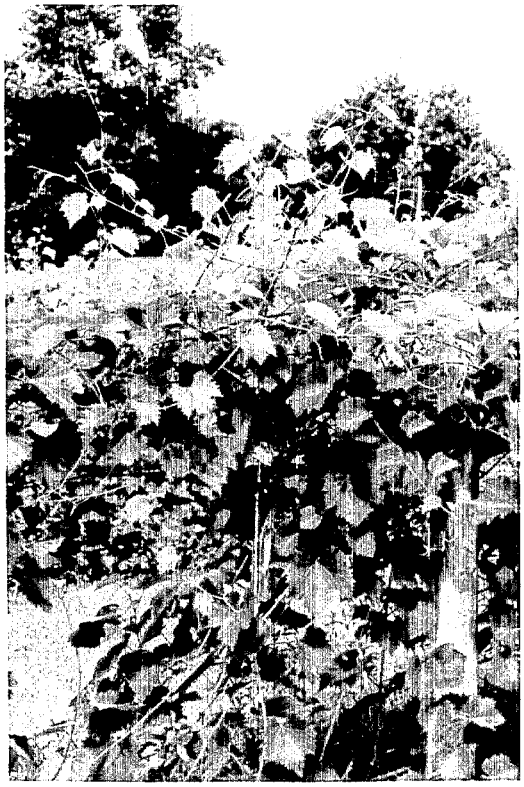
FIG. 1
FIG. 2
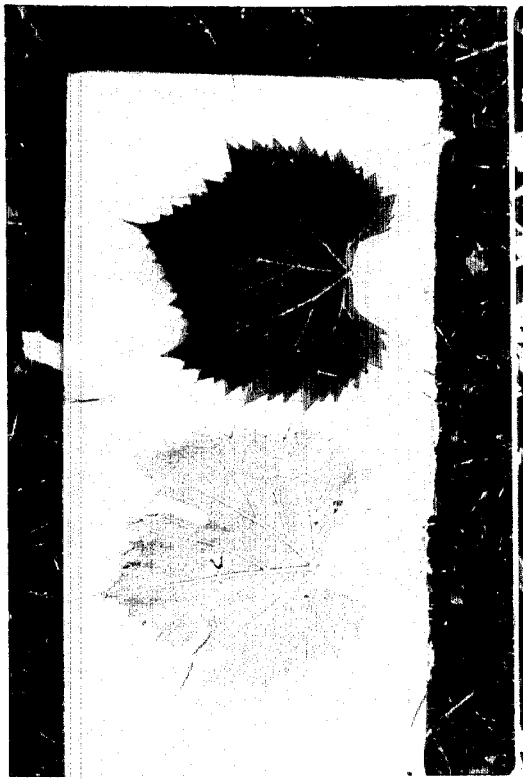
FIG. 3
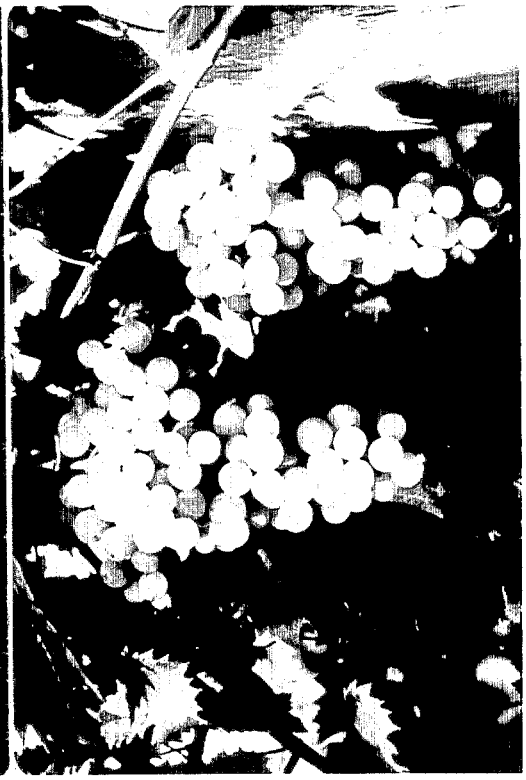

* * * * *